United States Patent [19]
Swaile

[11] Patent Number: 6,126,928
[45] Date of Patent: Oct. 3, 2000

[54] COMPOSITIONS CONTAINING SOLUBILIZED, ACID-ENHANCED ANTIPERSPIRANT ACTIVE

[75] Inventor: David Frederick Swaile, Cincinnati, Ohio

[73] Assignee: The Procter & Gamble Company, Cincinnati, Ohio

[21] Appl. No.: 09/382,417

[22] Filed: Aug. 24, 1999

[51] Int. Cl.[7] .............. A61K 7/32; A61K 7/34; A61K 7/38; A61K 7/00
[52] U.S. Cl. .............. 424/65; 424/66; 424/68; 424/400; 424/401
[58] Field of Search .................. 424/65, 66, 68, 424/400, 401

[56] References Cited

U.S. PATENT DOCUMENTS

| | | | |
|---|---|---|---|
| 3,420,932 | 1/1969 | Jones et al. | 424/47 |
| 3,901,711 | 8/1975 | Jones et al. | 423/462 |
| 3,928,545 | 12/1975 | Jones et al. | 423/463 |
| 4,435,382 | 3/1984 | Shin et al. | 424/66 |
| 4,704,271 | 11/1987 | Hourlhan et al. | 424/66 |
| 4,719,102 | 1/1988 | Randhawa et al. | 424/66 |
| 4,720,381 | 1/1988 | Schamper et al. | 424/66 |
| 4,767,875 | 8/1988 | Vincenti et al. | 666/176 |
| 4,781,917 | 11/1988 | Luebbe et al. | 424/65 |
| 5,179,220 | 1/1993 | Katsoulis et al. | 556/27 |
| 5,486,347 | 1/1996 | Callaghan et al. | 423/623 |
| 5,643,558 | 7/1997 | Provancal et al. | 424/66 |

FOREIGN PATENT DOCUMENTS

| | | | |
|---|---|---|---|
| 0 007 191 A1 | 1/1980 | European Pat. Off. | A61K 7/38 |
| 0 183 171 A2 | 6/1986 | European Pat. Off. | C01F 7/58 |
| 0 191 628 A2 | 8/1986 | European Pat. Off. | C01F 7/48 |
| 2 048 229 | 12/1980 | United Kingdom | C01F 7/48 |
| WO 96/33800 | 10/1996 | WIPO | B01F 17/42 |
| WO 97/34577 | 9/1997 | WIPO | A61K 7/32 |
| WO 98/58626 | 12/1998 | WIPO | A61K 7/38 |

*Primary Examiner*—Shelley A. Dodson
*Attorney, Agent, or Firm*—William J. Winter

[57] ABSTRACT

Disclosed are antiperspirant compositions which comprise from about 0.1% to about 50% by weight of solubilized antiperspirant active (e.g., aluminum-containing active or aluminum-zirconium containing active); and from about 0.1% to about 99.9% by weight of a liquid polyol having at least 2 hydroxyl groups, wherein 2 hydroxyl groups are attached to the α and β carbons of the liquid polyol and no more than 4 hydroxyl groups are attached to adjacent carbon atoms; a water-soluble, neutral amino acid; and a chlorine-containing inorganic acid; wherein the liquid polyol has a ClogP value of less than about 2.0, wherein the mole ratio of the neutral amino acid to the zirconium and aluminum is from about 0.09 to about 0.24, the mole ratio of the liquid polyol to the aluminum and zirconium is at least about 2.0:1, and the mole ratio of the zirconium and aluminum to chlorine is less than about 1.30:1. These antiperspirant compositions and corresponding methods of application provide improved antiperspirant efficacy, cosmetics, and mildness, and can prepared by simpler, more efficient, manufacturing methods. These compositions can also be used as base or intermediate materials to formulate other antiperspirant product forms providing similar performance benefits.

34 Claims, No Drawings

6,126,928

COMPOSITIONS CONTAINING SOLUBILIZED, ACID-ENHANCED ANTIPERSPIRANT ACTIVE

FIELD OF INVENTION

This invention relates to anhydrous compositions comprising solubilized, acid-enhanced antiperspirant active. These compositions provide improved mildness, cosmetics and antiperspirant efficacy as compared to many other polyol-containing antiperspirant compositions, and can be prepared by more efficient manufacturing methods.

BACKGROUND OF THE INVENTION

Polyol-containing carriers and solvents are well known for use in topical antiperspirant compositions. These carriers are most typically used to solubilize the antiperspirant active or as coupling agents during the manufacturing process. These polyol carriers are typically aliphatic polyhydric alcohols which have from 2 to 12 carbon atoms, examples of which include ethylene glycol, diethylene glycol, butylene glycol (1,3-butane-diol), 1,2-proplyene glycol, 1,3-propylene glycol, glycerine (1,2,3-trihydroxy propane), 2-methyl-2,4-pentane-diol (hexylene glycol), 2-ethyl-1,3-hexane-diol, 1,2,6-hexanetriol, 1,2,4-butanetriol, and combinations thereof.

Polyol-containing carriers are especially useful in formulating clear or translucent antiperspirant compositions. These compositions are typically anhydrous systems containing solubilized antiperspirant active, wherein the polyol carrier is used to help solubilize the active and in most cases provides the primary carrier material within which the solubilized active is miscible or dispersed within.

Many polyol-containing carriers, however, can cause skin irritation when topically applied to the underarms or other sensitive areas of the skin. This skin irritation is especially problematic when the applied composition is an anhydrous system containing higher concentrations of the polyol carrier. These higher polyol concentrations are often necessary in anhydrous antiperspirant compositions to successfully couple product gellants, structurants, thickening agents or other similar materials with other product carriers or solvents. This skin irritation, especially when caused by higher polyol concentrations, is especially problematic in a small percentage of the population that is unusually sensitive to topical polyol irritation. Although this type skin of irritation can be minimized by adding lower irritation solvents such as mineral oil or volatile silicones, these low irritation solvents are not miscible with higher concentrations of short carbon chain, highly polar, polyol solvents, e.g., dipropylene glycol, glycerin.

One recent attempt at providing improved polyol-containing carriers for use in antiperspirant products is described in U.S. patent application Ser. No. 09/071,178 (Swaile et al.) filed Jul. 27, 1999. The Swaile et al. Application discloses antiperspirant compositions containing 1,2-hexanediol, and the use of such compositions to provide improved mildness, cosmetics and antiperspirant efficacy.

It has now been found that polyol-containing carriers other than 1,2-hexanediol can also be selected for use in antiperspirant compositions which provide improved mildness, cosmetics and antiperspirant efficacy, provided that the selection is limited to those liquid polyols having at least 2 hydroxyl groups and preferably having at least 4 adjacent carbon atoms, wherein 2 of the hydroxyl groups are attached to the α and β carbons of the liquid polyol and no more than 4 hydroxyl groups are attached to adjacent carbon atoms, and wherein the liquid polyol has a ClogP value of less than about 2.0 and the mole ratio of the liquid polyol to the aluminum and zirconium is at least about 2.0:1.

It has also been found that the antiperspirant efficacy of these antiperspirant compositions can be improved by the addition of a water-soluble, neutral amino acid and chlorine-containing inorganic acid, provided that within the composition the mole ratio of the neutral amino acid to the zirconium and aluminum is from about 0.09 to about 0.24, the mole ratio of the liquid polyol to the aluminum and zirconium is at least about 2.0:1, and the mole ratio of the zirconium and aluminum to chlorine is less than about 1.30:1.

Although acid activated antiperspirant actives are known in the antiperspirant art, e.g., U.S. Pat. No. 4,331,609 (Orr), the art teaches that such acid-enhanced actives can be formulated as spray dried solids or solubilized in an aqueous medium, but it fails to teach formulation as an anhydrous composition containing solubilized acid enhanced active. It has now been found that these acid enhanced actives can be formulated as solubilized active in the anhydrous composition of the present invention. Using acid activated actives in these compositions improves manufacturing efficiency by relying upon acid activation rather than heat activation of the antiperspirant active. Heat activation processes are typically more expensive and require more manufacturing steps than acid activation processes.

SUMMARY OF THE INVENTION

The present invention is directed to anhydrous compositions comprising acid-enhanced antiperspirant active, and corresponding methods of application, which compositions comprise from about 0.1% to about 50% by weight of solubilized antiperspirant active; from about 0.1% to about 99.9% by weight of a liquid polyol having at least 2 hydroxyl groups and preferably having at least 4 adjacent carbon atoms, wherein 2 hydroxyl groups are attached to the α and β carbons of the liquid polyol and no more than 4 hydroxyl groups are attached to adjacent carbon atoms; a water-soluble amino acid; and a chlorine-containing inorganic acid; wherein the liquid polyol has a ClogP value of less than about 2.0, the mole ratio of the neutral amino acid to the zirconium and aluminum is from about 0.09 to about 0.24, the mole ratio of the liquid polyol to the aluminum and zirconium is at least about 2.0:1, and the mole ratio of the zirconium and aluminum to chlorine is less than about 1.30:1.

It has been found that these anhydrous, acid-enhanced, antiperspirant compositions, and corresponding methods of application, provide improved antiperspirant efficacy, cosmetics, and are milder to the skin, provided that the liquid polyol has the requisite number and arrangement of hydroxyl groups, and provided that the liquid polyol also has a ClogP value of less than about 2.0 and is used in the requisite mole ratio relative to the antiperspirant metal ions in the composition.

It has also been found that these anhydrous antiperspirant compositions can be formulated with solubilized, acid-enhanced antiperspirant active. These acid-enhanced actives can be formulated as solubilized active in the anhydrous composition of the present invention. Using acid activated actives in these compositions improves manufacturing efficiency by relying upon acid activation rather than heat activation of the antiperspirant active. Heat activation processes are typically more expensive and require more manufacturing steps than acid activation processes, prepared by more efficient manufacturing methods than many prior art methods for making solubilized, enhanced antiperspirant active, provided that the antiperspirant composition also contains a combination of a water-soluble amino acid and a chlorine-containing inorganic acid.

DETAILED DESCRIPTION

The antiperspirant compositions of the present invention include antiperspirant compositions in final, intermediate, or base forms, and include product forms such as solids or gel solid sticks, soft solids or creams, lotions or other liquids, aerosol or pump sprays, solutions or dispersions, and so forth. These antiperspirant compositions are intended for topical application to the underarm or other suitable area of the skin, or for formulation into topical underarm products that are likewise intended for similar application.

The term "anhydrous" as used herein, unless otherwise specified, characterizes the water content of the compositions and corresponding ingredients of the present invention, and means that these compositions and ingredients so characterized contain contain less than about 20%, more preferably less than about 10%, even more preferably less than about 5%, by weight of water.

The term "ambient conditions" as used herein refers to surrounding conditions under about one atmosphere of pressure, at about 50% relative humidity, and at about 25° C.

The term "volatile" as used herein refers to those materials which have a measurable vapor pressure as measured at 25° C. Such vapor pressures will typically range from about 0.01 mmHg to about 6 mmHg, more typically from about 0.02 mmHg to about 1.5 mmHg, and have an average boiling point at one atmosphere of pressure (1 atm) typically less than about 250° C., more typically less than about 235° C., at 1 atmosphere (atm) of pressure.

The term "aluminum and zirconium" as used herein, unless otherwise specified, means aluminum, or it means the combination of aluminum and zirconium in those embodiments optionally containing zirconium.

The term "metal" as used herein, unless otherwise specified, means the combination of aluminum and optional zirconium in the anhydrous composition of the present invention.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions and corresponding methods of application of the present invention can comprise, consist of, or consist essentially of the essential elements and limitations of the invention described herein, as well as any of the additional or optional ingredients, components, or limitations described herein.

Selected Polyols

The antiperspirant compositions of the present invention comprises selected polyols for solubilizing or helping to solubilize the antiperspirant active material in the composition. The antiperspirant composition comprises from about 0.1% to about 99.9%, preferably from about 5% to about 80%, more preferably from about 10% to about 60%, by weight of the selected liquid polyols.

The selected liquid polyols for use in the antiperspirant composition of the present invention have 2 or more hydroxyl groups with 2 of the hydroxyl groups attached to the $\alpha$ and $\beta$ carbons of the liquid polyol, and no more than 4 adjacent hydroxyl groups. The selected polyols preferably have from about 3 to about 8, more preferably from about 4 to about 10 adjacent carbon atoms, and preferably having either 2 or 3 hydroxyl groups in total.

The selected liquid polyols for use in the antiperspirant compositions of the present invention must be formulated into the composition so that the resulting mole ratio of the selected liquid polyols to the combination of zirconium and aluminum ions is at least about 2.0, preferably at least about 2.5, most preferably at least about 3.0. It has been found that the concentration of antiperspirant active solubilized into the liquid polyols is dependent upon this mole ratio of the selected 1,2-diols to antiperspirant metal ions (zirconium and aluminum). Solutions with a mole ratio of selected polyols to antiperspirant metal ions of less than about 2.0 are unstable and will easily precipitate during the manufacturing process or during storage, so that the maximum concentration of active that can be used to make a stable solution is dependent upon the molecular weight of the selected polyol solvent, the number of 1,2 diol functional groups per molecule, and the aluminum to zirconium ratio making up the active.

The selected polyols for use in the antiperspirant compositions of the present invention must also have a ClogP value of less than about 2.0, preferably from about −4.0 to about 2.0, more preferably from about −4.0 to about 1.0, even more preferably from about −2.0 to about 1.0, even more preferably from about −1.0 to about 0.5. It has been found that the selection of the liquid polyols as defined by ClogP values provides the selected polyol with optimal active release characteristics at the appropriate time after topical application to the underarm. It has been found that the active release characteristics such as that provided by the selected polyols helps provide the composition with improved antiperspirant efficacy.

The ClogP value (calculated logP) as used herein helps define selection of the liquid polyol component of the present invention. For purposes of defining and selecting the appropriate liquid polyol, the ClogP values are calculated for each liquid polyol by the Pamona Med Chem/Daylight "CLOGP" program, Version 4.42, available from Biobyte Corporation, Claremont, Calif. Other suitable methods for determining ClogP values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, California, Daylight V4.61, Algorithm: V3.05, Database: V16. General information pertaining to ClogP values and methodologies are described in Chemical Reviews, 93(4), 1993, 1281–1306, which description is also incorporated herein by reference.

Suitable liquid polyols for use herein include any polyol material that is liquid under ambient conditions, or which is otherwise in liquid form within the selected composition, and has the requisite number and arrangement of hydroxyl groups and has the requisite ClogP value as defined herein.

Generally, the preferred polyols for selection and use in the composition of the present invention include alkyl diols, glycerol ethers and other polyol liquids, which correspond to the formula:

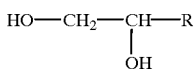

wherein the preferred polyols must have the requisite ClogP and hydroxyl group arrangement as described herein for all selected polyols, and wherein R is an alkyl (C2 or higher), ether, ester, amine or combination thereof. The R group cannot be hydrogen, methyl or hydroxyethyl. The R group can be substituted or unsubstituted, branched or straight or cyclic, saturated or unsaturated. The R group is preferably an alkyl group having from 2 to 6 carbon atoms, or any substituted group having 4 or more carbon atoms (e.g., hydroxy substituted, ethoxylates, propoxylates). Non limiting examples of suitable substituents include hydroxyl groups, amines, amides, esters, ethers, alkoxylate groups (e.g., ethoxylates, propoxylates, etc.) and so forth.

Preferred alkyl diols and polyols for selection and use in the composition of the present invention include those which correspond to the formula:

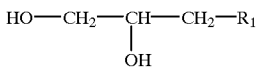

wherein the alkyl diol and polyol liquids must have the requisite ClogP and hydroxyl group arrangement as described herein for all selected polyols, and wherein $R_1$ is a substituted or unsubstituted, branched or straight or cyclic, saturated or unsaturated, hydrocarbon moiety. $R_1$ is preferably a methyl group or an alkyl group having from 3 to 5 carbon atoms, or any substituted group having 3 or more carbon atoms (e.g., hydroxy substituted, polyethoxylates, polypropoxylates). Non limiting examples of suitable substituents include hydroxyl groups, amines, amides, esters, ethers, alkoxylate groups (e.g., ethoxylates, propoxylates, etc.) and so forth.

Examples of suitable alkyl diols, and their corresponding ClogP values, for use in the composition include 1,2-butanediol (−0.53), 1,2-pentanediol (0.0), 4-methyl-1,2-pentanediol (0.397), 2-methyl-1,2-pentanediol (0.399), 3,3-methyl-1,2-butanediol (0.267), 4-methyl-1,2-hexanediol (0.926), 1,2-heptanediol (1.056), 3-phenyl-1,2-propanediol (0.508), and combinations thereof.

Preferred glycerol ether liquids for selection and use in the composition of the present invention include those which correspond to the formula:

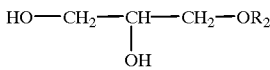

wherein the glycerol ether liquids must have the requisite ClogP and hydroxyl group arrangement as described herein for all selected polyols, and wherein $R_2$ is a substituted or unsubstituted, branched or straight or cyclic, saturated or unsaturated, hydrocarbon moiety. The $R_2$ group is preferably selected from alkyl groups having from 1 to 5 carbon atoms, or substituted groups containing 2 or more carbon atoms (e.g., hydroxy substituted, ethoxylates, propoxylates). Non limiting examples of suitable substituents include hydroxyl groups, amines, amides, esters, ethers, alkoxylate groups (e.g., ethoxylates, propoxylates, etc.) and so forth.

Suitable glycerol ethers and their respective ClogP values include glycerol isopropyl ether (−0.51), glycerol propyl ether (−0.73), glycerol ethyl ether (−1.04), glycerol methyl ether (−1.57), glycerol butyl ether (0.01), glycerol isopentyl ether (0.41), diglycerol isopropyl ether (−1.49), diglycerol isobutyl ether (−0.96), diglycerol (−2.95), triglycerol (−3.71), triglycerol isopropyl ether (−2.25), and combinations thereof.

Other suitable polyol liquids and their respective ClogP values include acetic acid glycerol ester (−1.30), propanoic acid glycerol ester (−0.77), butanoic acid glycerol ester (−0.24), 3-methyl butanoic acid glycerol ester (0.16) and 3-trimethylsily-1,2-propane diol (0.56) and combinations thereof.

Other preferred polyols include 1,2,6-hexanetriol; 1,2-hexanediol; 1,2,4-butanetriol; propylene glycol; glycerine; ethylene glycol; and combinations thereof, more preferably 1,2-hexanediol.

These selected polyols are formulated into the antiperspirant composition alone or preferably in combination with one or more other liquid carriers, examples of such other liquid carriers include any known or otherwise effective carrier liquid suitable for topical application to the skin which is also compatible with the solubilized antiperspirant active component of the composition. Such other optional liquid carriers are preferably anhydrous.

Solubilized Antiperspirant Active

The antiperspirant compositions of the present invention comprise from about 0.1% to about 50% by weight of a solubilized antiperspirant active suitable for application to human skin. The concentration of antiperspirant active in the composition should be sufficient to provide the finished antiperspirant product with the desired perspiration wetness and odor control.

The antiperspirant compositions of the present invention preferably comprise, or provide finished product that comprises, solubilized antiperspirant active at concentrations of from about 0.1% to about 35%, preferably from about 3% to about 20%, even more preferably from about 4% to about 19%, by weight of the composition. All such weight percentages are calculated on an anhydrous metal salt basis exclusive of water and any complexing or buffering agent, including any water-soluble amino acids as described herein, e.g., glycine.

The solubilized antiperspirant active for use in the antiperspirant compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

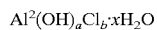

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant compositions include those which conform to the formula:

$$ZrO(OH)_{2-a}Cl_a \cdot xH_2O$$

wherein a is any number having a value of from about 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, one of the water-soluble neutral amino acids described herein, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

It has been found that the anhydrous antiperspirant compositions of the present invention, which all contain solubilized antiperspirant active, provide good application and aesthetic characteristics, and relative to other solubilized active compositions, are typically less sticky during or after application and are milder to the skin. It has also been found that solutions of solubilized antiperspirant active and the selected polyol as defined herein are more compatible with nonpolar solvents, even when the latter is used at higher concentrations. This now allows for the formulation of clear or translucent antiperspirant compositions containing nonpolar solvents such as volatile and nonvolatile silicones.

Acid Activation

The anhydrous antiperspirant compositions of the present invention comprise a combination of a water-soluble, neutral amino acid and a chlorine-containing inorganic acid.

Neutral, water-soluble amino acids for use in the composition of the present invention are those which contain an equal number of amino and carboxyl groups (e.g., neutral charge) and which are readily soluble in water, e.g. water solublity of greater than about 0.2 grams/ml. Preferred neutral, water-soluble amino acids are alanine, β-alanine, methionine, tryptophan, β-phenylalanine, serine, valine, glycine, 2-amino-butyric acid, and combinations thereof. Most preferred is glycine.

The neutral, water-soluble amino acid is preferably added to the anhydrous composition of the present invention such that the molar ratio of the neutral amino acid to total metal (zirconium and aluminum) in the composition is from about 0.09 to about 0.24, more preferably from about 0.13 to about 0.20. The neutral amino acid forms a soluble complex with the antiperspirant active metals (zirconium and aluminum) in the composition.

The chlorine-containing inorganic acids are added at varied concentrations and amounts depending upon the other ingredients in the composition. All of these concentrations and amounts, however, must still provide the composition with a mole ratio of the total metal (zirconium and aluminum) to chlorine of less than about 1.30, preferably from about 0.80 to about 1.30, even more preferably from about 1.0 to about 1.30. This range of metal to chlorine molar ratios is important in formulating the anhydrous compositions of the present invention because, when the composition is formulated and applied topically in its final product form, molar ratios above about 1.30 can result in reduced antiperspirant efficacy and molar ratios below about 0.8 can result in excessive skin irritation. Preferred chlorine-containing inorganic acids for use in the composition of the present invention include hydrochloric acid, aluminum chloride, and combinations thereof.

Optional Ingredients

The antiperspirant compositions of the present invention may further comprise one or more optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Nonlimiting examples of optional ingredients suitable for use in the antiperspirant compositions herein include pH buffering agents; other solid or liquid carriers; emollients; humectants; soothing agents; wash-off aids; residue masking agents; dyes and pigments; medicaments; baking soda and related materials; preservatives; and so forth.

Optional Liquid Carriers

In addition to the selected polyol liquids described herein, the antiperspirant composition preferably further comprises one or more optional liquid carriers suitable for topical application and appropriate for the product form desired. Such other optional carriers include any known or otherwise effective liquid carrier material for use in antiperspirants, deodorants or other topical compositions. In the event that the optional liquid carrier is not readily miscible or dispersible in the selected polyol liquid or with other optional carriers in the composition, then other liquid carriers or coupling agents may be added to the composition to bring the selected polyol liquid and other immiscible or nondispersible materials (e.g., nonpolar solvents) into a homogenous solution or dispersion.

Optional liquid carriers include any topically safe and effective organic or silicone-containing, volatile or non-volatile, polar or non-polar carrier liquid, provided that the resulting combination of carrier materials forms a solution or other homogenous liquid or liquid dispersion at the selected processing temperature of the composition, or which otherwise form a clear or translucent emulsion or suspension. Processing temperatures for the antiperspirant compositions typically range from about 28° C. to about 250° C., more typically from about 28° C. to about 110° C., and even more typically from about 28° C. to about 100° C. Examples of suitable optional carrier liquids, and other optional ingredients suitable for use herein, are described in U.S. Pat. Nos. 5,902,570 (Bretzler et al.); 5,750,096 (Guskey); and 5,916,546 (Sawin et al.), which descriptions are incorporated herein by reference.

Preferred optional carrier liquids include volatile silicones in combination with the selected polyol liquid. The concentration of the volatile silicone preferably ranges from about 10% to about 90%, more preferably from about 15% to about 65%, by weight of the antiperspirant composition. These volatile silicone carriers may be cyclic, linear or branched chain silicones having the requisite volatility defined herein. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

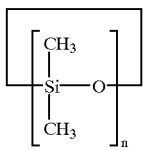

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corningy 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

Other optional liquid carriers may also include a non-volatile, solid or liquid, silicone carrier. These non-volatile silicone carriers are preferably liquids, and are preferably linear silicones which include, but are not limited to, those which conform to either of the formulas:

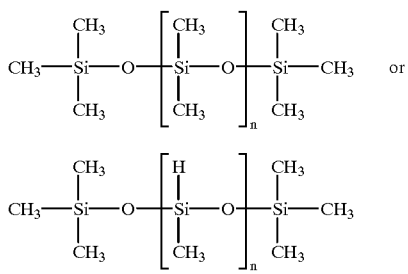

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The antiperspirant composition preferably comprises a combination of volatile and nonvolatile silicone materials, more preferably a combination of volatile and nonvolatile silicone carrier liquids. Nonlimiting examples of suitable combinations of such silicone materials are described in U.S. Pat. No. 5,156,834 (Beckmeyer et al.), which descriptions are incorporated herein by reference.

Other optional carriers for use in combination with the selected polyol liquid may also include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Preferably such optional liquid carriers are also water-immiscible liquids under ambient conditions. Other suitable water-immiscible, polar organic liquid carriers or solvents for use in combination with the selected polyol liquid are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other optional liquid carriers for use in combination with the selected polyol liquid include anhydrous, water-miscible, polar organic liquid carriers or solvents, examples of which include short chain alcohols such as ethanol and glycol solvents such as propylene glycol, hexylene glyol, dipropylene glycol, tripropylene glycol, and so forth. Other suitable similar solvents also include polyalkoxylated carriers such as polyethylene glycols, polypropylene glycols, combinations and derivatives thereof, and so forth. Nonlimiting examples of polar solvents suitable for use herein are described in U.S. Pat. No. 5,429,816, which description is incorporated herein by reference. Other suitable polar solvents include phthalate co-solvents, benzoate co-solvents, cinnamate esters, secondary alcohols, benzyl acetate, phenyl alkane and combinations thereof.

Optional liquid carriers for use in combination with the selected polyol liquid may also include non-polar carriers such as mineral oil, petrolatum, isohexadecane, isododecane, various hydrocarbon oils such as the Isopar or Norpar series available from Exxon Corp. or Permethyl series available from Persperse, and the Soltrol series available from Phillips Chemical, and any other polar or non-polar, water-miscible, organic carrier liquid or solvent known or otherwise safe and effective for topical application to human skin.

Optional Suspending or Thickening Agent

The antiperspirant compositions of the present invention may further comprise a suspending or thickening agent to help provide the composition with the desired viscosity or product hardness, or to otherwise help suspend any dispersed solids or liquids within the composition. Suitable suspending or thickening agents include any material known or otherwise effective in providing suspending or thickening properties to the composition, or which otherwise provide structure to the final product form. These suspending or thickening agents include gelling agents, and polymeric or nonpolymeric or inorganic thickening or viscosifying agents. Such materials will most typically include organic solids, silicone solids, crystalline or other gellants, inorganic particulates such as clays or silicas, or combinations thereof.

The concentration and type of optional suspending or thickening agent selected for use in the antiperspirant composition will vary depending upon the desired product form, viscosity, and hardness. For most suspending or thickening agents suitable for optional use herein, the concentration of such suspending or thickening agents will most typically range from about 0.1% to about 35%, more typically from about 0.1% to about 20%, by weight of the composition.

Suitable gelling agents for use as optional suspending or thickening agents in the antiperspirant composition include, but are not limited to, fatty acid gellants, hydroxy acid gellants, esters and amides of fatty acid or hydroxy fatty acid gellants, cholesterolic materials, dibenzylidene alditols, lanolinolic materials, and other amide and polyamide gellants.

Suitable gelling agents include fatty alcohols having from about 8 to about 40 carbon atoms, preferably from 8 to about 30 carbon atoms, more preferably from about 12 to about 18 carbon atoms. These gelling agents are wax-like materials which are most typically used at concentrations ranging from about 1% to about 25%, preferably from about 5% to about 20%, most preferably from about 10% to about 20%, by weight of the antiperspirant composition. Preferred are cetyl alcohol, myristyl alcohol, stearyl alcohol and combinations thereof, more preferably stearyl alcohol.

Other suitable gelling agents include waxes or wax-like materials having a melt point of above 65° C., more typically from about 65° C. to about 130° C., examples of which include, but are not limited to, waxes such as beeswax, carnauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792, Elsnau, issued September 20, 1977, which description is incorporated herein by reference.

Other suitable gelling agents include fatty acid gellants such as fatty acid and hydroxy or alpha hydroxy fatty acids, having from about 10 to about 40 carbon atoms, and esters and amides of such gelling agents. Nonlimiting examples such gelling agents include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are esters of 12-hydroxystearic acid, amides of 12-hydroxystearic acid and combinations thereof, and all other gelling agents which correspond to the following formula:

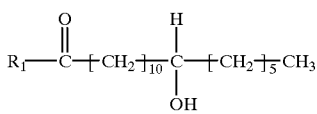

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof.

Suitable amide gellants include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, apartic acid, and combinations thereof. Other suitable amide gelling agents are described in U.S. Pat. No. 5,429,816, issued Jul. 4, 1995, and U.S. patent application Ser. No. 08/771,183, filed Dec. 20, 1996, which descriptions are incorporated herein by reference. Concentrations of all such gelling agents preferably range from about 0.1% to about 25%, preferably of from about 1% to about 15%, more preferably from about 1% to about 10%, by weight of the antiperspirant composition.

Other suitable gelling agents include triglyceride gellant systems which comprise glyceryl tribehenate and other triglycerides, wherein at least about 75%, preferably about 100%, of the esterified fatty acid moieties of said other triglycerides each have from about 18 to about 36 carbon atoms, and wherein the mole ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant material preferably has a melting point of at less than about 110° C., preferably between about 50° C. and 110° C.

Preferred concentrations of the above-described triglyceride gellant systems range from about 0.1% to about 20%, more preferably from about 0.5% to about 15%, by weight of the antiperspirant composition. For roll-on formulations having a penetration force value of from about 20 gram-force to about 100 gram. force, triglyceride concentrations preferably range from about 1% to about 5% by weight of the antiperspirant composition. For other cream formulations, including those formulations suitable for use in cream applicator devices, which have a penetration force value of from about 100 gram-force to about 500 gram-force, triglyceride concentrations preferably range from about 4% to about 20%, more preferably from about 4% to about 10%, by weight of the antiperspirant composition. Specific examples of triglyceride gelling agents for use in the antiperspirant compositions that are commercially available include, but are not limited to, tristearin, hydrogenated vegetable oil, trihydroxysterin (Thixcin® R, available from Rheox, Inc.), rape seed oil, castor wax, fish oils, tripalmiten, Syncrowax® HRC and Syncrowax® HGL-C (Syncrowax® available from Croda, Inc.).

Other suitable suspending or thickening agents for use in the antiperspirant composition include particulate suspending or thickening agents such as clays and colloidal pyrogenic silica pigments. Other known or otherwise effective particulate suspending or thickening agents can likewise be used in the antiperspirant composition. Concentrations of optional particulate thickening agents preferably range from about 0.001% to about 15%, more preferably from about 1% to about 15%, even more preferably from about 1% to about 8%, by weight of the composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Nonlimiting examples of suitable clay activators include propylene carbonate, ethanol, and combinations thereof. The amount of clay activator will typically range from about 25% to about 75% by weight of the clay, more typically from about 40% to about 60% by weight of the clay.

Optional Deodorant Active and Fragrance

The antiperspirant compositions of the present invention may further comprise a deodorant active, fragrance or combination thereof at concentrations ranging from about 0.001% to about 50%, preferably from about 0.01% to about 20%, more preferably from about 0.1% to about 10%, by weight of the composition. These deodorant actives and perfumes may be used in addition to or in place of some or all of the antiperspirant active material, and include any known or otherwise safe and effective deodorant or fragrance suitable for topical application to human skin.

Deodorant actives suitable for use in the composition of the present invention includes any topical material that is known for or is otherwise effective in preventing or eliminating malodor associated with perspiration, other than those active materials described hereinbefore. These deodorant actives are typically antimicrobial agents (e.g., bacteriocides, fungicides), malodor-absorbing material, or combinations thereof.

Preferred deodorant actives are antimicrobial agents, Nonlimiting examples of which include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether, 3,4,4'-trichlorocarbanilide, diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Other optional deodorant actives include odor-absorbing materials such as carbonate and bicarbonate salts, including alkali metal carbonates and bicarbonates, ammonium and tetraalkylammonium Preferred are sodium and potassium salts of such odor-absorbing materials.

The antiperspirant composition of the present invention may optionally comprise fragrances suitable for use in a topical composition, and includes any topical material that is known for or is otherwise effective in masking malodor associated with perspiration, or which otherwise provides the composition with the desired perfumed aroma. These fragrances include any perfume or perfume chemical suitable for topical application to the skin.

The concentration of the optional fragrance should be effective to provide the desired aroma characteristics or to mask malodor, wherein the malodor is inherently associated with the composition itself or is associated with malodor development from human perspiration. Also, the fragrance and whatever carriers accompany it preferably do not impart excessive stinging to the skin, especially broken or irritated skin, at the levels previously disclosed. The fragrance will typically be in the form of water insoluble perfumes that are solubilized in the matrix of the composition.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-annelid-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable but optional fragrances are those which mask or help to mask odors associated with perspiration (hereinafter referred to as odor masking fragrances), some nonlimiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The optional fragrance may also contain solubilizers, diluents, or solvents which are well known in the art. Such materials are described in Arctander, Perfume and Flavour Chemicals (Aroma Chemicals), Vol. I and II (1969).

Method of Manufacture

The compositions of the present invention may be made by methods known in the art for formulating anhydrous compositions containing solubilized antiperspirant active, or which are otherwise effective in formulating such compositions. As will be apparent to those skilled in the art, the particular method will be dependent upon the selection of the specific types and amounts of the components employed, as well as the desired product form, e.g., solid, semi-solid, liquid, solution or suspension, finish product or manufacturing intermediate, etc.

The antiperspirant compositions of the present invention is preferably prepared by combining in water or other suitable aqueous system antiperspirant active (e.g., aluminum chlorohydrate, zirconyl hydroxy chloride), neutral amino acid (e.g., glycine) and inorganic acid under the appropriate process conditions, to thus produce an aqueous composition containing acid-activated antiperspirant active. For acid-activation to occur, it is important that these ingredients, or at least the inorganic acid and antiperspirant active, be combined in water or other suitable aqueous system. Acid activation will not typically occur outside an aqueous system. These ingredients are combined in the water or aqueous system at temperatures below about 140° C., preferably at temperatures of from about 20° C. to about 100° C., so that the added antiperspirant active is rendered solubilized in the aqueous solution. Total antiperspirant active concentrations in the aqueous solution during processing will typically be less than about 60%, preferably from about 20% to about 50%, even more preferably from about 25% to about 40%, by weight of the composition. The liquid polyol is then added to the aqueous, acid-activated, solubilized antiperspirant active, solution and then the resulting composition is subjected to any suitable water removal step or sequence to produce an anhydrous liquid containing the solubilized, acid-enhanced, antiperspirant active.

Examples of methods of making anhydrous compositions containing antiperspirant active, including water removal steps suitable for use herein, are described in U.S. Pat. No. 4,781,917 (Luebbe et al.), U.S. Pat. No. 5,643,558 (Provancal et al.), and European Patent Application 0 404 533 A1 (Smith et al.), which patents are incorporated herein by reference.

To formulate a solid or soft solid product, the antiperspirant active is preferably dissolved or maintained as such by the addition of the selected polyol, neutral amino acid, and inorganic acid, and any optional liquid carriers or cosolvents at a processing temperature of up to about 130° C., typically at a temperature of from about 20° C. to about 130° C. Optional suspending agents are added to the heated mixture, and the heating process maintained until the heated liquid appears to be clear and homogenous, which will typically occur for most combinations at a temperature of between about 60° C. and about 130° C. The resulting clear liquid is then cooled or allowed to cool to between about 40° C. and about 120° C., at which time any other optional ingredients are then added to and mixed with the cooled liquid. The resulting liquid solution or mixture is then poured into containers and allowed to cool further and solidify to the desired product hardness. Alternatively, many of these optional ingredients can be added along with the liquid carriers during the initial heating sequence, or at any other time that is suitable for such addition in order to manufacture the desired product form.

To formulate an aerosol, roll-on or other liquid formulation, any known or otherwise effective manufacturing or formulation method can be use to formulate the antiperspirant compositions in such product forms.

Nonlimiting examples of suitable methods for manufacturing the antiperspirant compositions of the present invention are also described in U.S. Pat. No. 5,429,816 (Hofrichter et al.); U.S. Pat. No. 5,733,534 (Sawin et al.); U.S. Pat. No. 5,605,681 (Trandai et al.); U.S. Pat. No. 5,346,694 (Juneja); U.S. Pat. No. 5,298,236 (Orr et al.); and U.S. Pat. No. 5,718,890 (Putnam et al.), which descriptions are incorporated herein be reference.

Method For Use

The antiperspirant composition of the present invention may be used as a manufacturing intermediate in formulating other antiperspirant compositions, or it may be formulated in final form to be topically applied to the axilla or other area of the skin in any known or otherwise effective method for controlling malodor associated with perspiration. These methods comprise applying to the axilla or other area of the human skin a safe and effective amount of the antiperspirant composition of the present invention. In this context, the term "safe and effective amount" means an amount of the antiperspirant composition topically applied to the skin which is effective in inhibiting or minimizing masking, perspiration at the site of application while also being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or more times daily, preferably once daily.

EXAMPLES

The following Examples illustrate specific embodiments of the antiperspirant compositions of the present invention, including methods of manufacture and use, but are not intended to be limiting thereof. Other modifications can be undertaken by the skilled artisan without departing from the spirit and scope of this invention.

The exemplified compositions are applied topically to the underarm in an amount effective to inhibit or prevent perspiration in humans, typically an amount which ranges from about 0.1 gram to about 2 grams per axilla. The applied compositions are effective in inhibiting perspiration from the applied areas, and have good skin feel characteristics during and after application. The applied compositions are milder to the skin and cause little or no skin irritation. All exemplified amounts are weight-weight percents based on the total weight of the composition, unless otherwise specified.

The antiperspirant compositions of the present invention include final and intermediate product forms, and such forms can have a wide range of viscosity and physical characteristics depending on whether the product is in solid, semi-solid or liquid form, or is otherwise formulated as a solution, suspension, dispersion, etc. Nonlimiting working examples of some of these product forms are described hereinafter.

Example 1

In one embodiment of the present invention, an anhydrous antiperspirant composition is formulated by mixing under ambient temperatures in an aqueous system aluminum chlorohydrate (663 parts of about a 50% aqueous solution, non-activated active, 12.7% Al, 8.0% Cl), zirconyl hydroxy chloride (693 parts of about a 50% aqueous solution, 13.8% Zr, 5.6% Cl), glycine (60 parts) and $AlCl_3 \cdot 6 H_2O$ (84 part 43.6% Cl) to form an aqueous solution containing acid-activated aluminum-zirconium antiperspirant active. The resulting aqueous solution which now contains an acid-activated aluminum-zirconium antiperspirant active is mixed under ambient temperatures with 1,2-hexanediol at a weight ratio of the 1,2-hexanediol to the aqueous solution of 1.06. Water is then removed from the aqueous solution via vacuum distillation at a temperature ranging from about 20°

C. to about 100° C. (temperature varies with selected distillation pressure). The resulting composition is an anhydrous composition of the present invention that comprises about 31.7% by weight of activated aluminum zirconium antiperspirant active (calculated on an anhydrous, unbuffered basis), about 3.7% by weight of glycine (calculated as part of an aluminum-zirconium complex), about 58% by weight of 1,2-hexanediol, and less than about 7% by weight of water, wherein the composition has a metal to chloride mole ratio of 1.2, an aluminum to zirconium mole ratio of 3.3, a zirconium to chloride (in zirconyl hydroxy chloride) mole ratio of 1.0, a glycine to metal mole ratio of 0.18, and a 1,2-hexanediol to metal mole ratio of 3. The acid-activated aluminum-zirconium antiperspirant active remains solubilized in the anhydrous composition.

The resulting composition is a clear or translucent, anhydrous liquid that is used as a manufacturing intermediate to make other products or is used as a topical liquid delivered from an appropriate package, e.g., roll-on applicator, by the application methods described herein.

Example 2

In yet another embodiment of the present invention, an anhydrous antiperspirant composition is formulated by mixing under ambient temperatures in an aqueous system aluminum chlorohydrate (712 parts of about a 50% aqueous solution, non-activated active, 12.7% Al, 8.0% Cl), zirconyl hydroxy chloride (659 parts of about a 50% aqueous solution, 13.8% Zr, 5.6% Cl)), glycine (61 parts) and HCl (68 parts of about a 37.6% aqueous solution) to form an aqueous solution containing acid-activated aluminum-zirconium antiperspirant active. The resulting aqueous solution which now contains an acid-activated aluminum-zirconium antiperspirant active is mixed under ambient temperatures with isopropyl glycerol ether at a weight ratio of the isopropyl glycerol ether to the aqueous solution of 1.24. Water is then removed from the aqueous solution via vacuum distillation at a temperature ranging from about 20° C. to about I00° C. (temperature varies with selected distillation pressure).

The resulting composition is an anhydrous composition of the present invention that comprises about 25.8% by weight of activated aluminum zirconium antiperspirant active (calculated on an anhydrous, unbuffered basis), about 3.2% by weight of glycine (calculated as part of an aluminum-zirconium complex), about 64% by weight of isopropyl glycerol ether, and less than about 7% by weight of water,, wherein the composition has a metal to chloride mole ratio of 1.29–1.30, an aluminum to zirconium mole ratio of 3.4, a zirconium to chloride (in zirconyl hydroxy chloride) mole ratio of 1.0, a glycine to metal mole ratio of 0.18, and a isopropyl glyercerol ether to metal mole ratio of 3. The acid-activated aluminum-zirconium antiperspirant active remains solubilized in the anhydrous composition.

The resulting composition is a clear or translucent, anhydrous liquid that is used as a manufacturing intermediate to make other products or is used as a topical liquid delivered from an appropriate package, e.g., roll-on applicator, by the application methods described herein.

What is claimed is:

1. An anhydrous antiperspirant composition comprising:
   A) from about 0.1% to about 99.9% by weight of a liquid polyol having at least 4 adjacent carbon atoms and at least two hydroxyl groups, wherein 2 of the hydroxyl groups are attached to the α and β carbons of the liquid polyol and no more than 4 of the hydroxyl groups are attached to adjacent carbon atoms, and wherein the liquid polyol has a C log P value of from about –4.0 to about 2.0;
   B) from about 0.1% to about 50% by weight of solubilized antiperspirant active selected from aluminum containing antiperspirant active and aluminum-zirconium containing antiperspirant active;
   C) a water-soluble, neutral amino acid; and
   D) a chlorine-containing inorganic acid;
   wherein the mole ratio of the neutral amino acid to the zirconium and aluminum is from about 0.09 to about 0.24, the mole ratio of the liquid polyol to the aluminum and zirconium is at least about 2.0:1, and the mole ratio of the zirconium and aluminum to chloride is less than about 1.30:1.

2. The anhydrous antiperspirant composition of claim 1 wherein the water soluble amino acid is glycine.

3. The antiperspirant composition of claim 1 wherein the antiperspirant active is an aluminum-containing antiperspirant active, and the chlorine-containing inorganic acid is selected from the group consisting of aluminum chloride, hydrochloric acid and combinations thereof.

4. The antiperspirant composition of claim 3 wherein the antiperspirant active is selected from the group consisting of aluminum containing active, aluminum-zirconium containing active, and thereof, wherein the mole ratio of the liquid polyols to the aluminum and zirconium is at least about 2.0:1.

5. The antiperspirant composition of claim 4 wherein the mole ratio of the liquid polyol to the aluminum and zirconium is at least about 3.0:1.

6. The antiperspirant composition of claim 1 wherein the liquid polyol has from about 4 to about 8 adjacent carbon atoms.

7. The antiperspirant composition of claim 1 wherein the liquid polyol is a 1,2 alkyl diol having from about 4 to about 8 adjacent carbon atoms.

8. The antiperspirant composition of claim 1 wherein the liquid polyol comprises a glycerol ether selected from the group consisting of glycerol isopropyl ether, glycerol propyl ether, glycerol ethyl ether, glycerol methyl ether, glycerol butyl ether, glycerol isopentyl ether, diglycerol isopropyl ether, diglycerol isobutyl ether, diglycerol, triglycerol, triglycerol isopropyl ether, and combinations thereof.

9. The antiperspirant composition of claim 8 wherein the liquid polyol is isopropyl glycerol ether.

10. The antiperspirant composition of claim 7 wherein the 1,2-alkyl diol is selected from the group consisting of 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 2-phenyl-1,2-propanediol; 1,2-glycerin; 1,2,4-butanetriol; 1,2,6-hexanetriol, and combinations thereof.

11. The antiperspirant composition of claim 1 wherein the liquid polyol is selected from the group consisting of acetic acid glycerol ester, propanoic acid glycerol ester, butanoic acid glycerol ester, 3-methyl butanoic acid glycerol ester and 3-trimethylsily-1,2-propane diol and combinations thereof.

12. The antiperspirant composition of claim 1 wherein the ClogP value is from about –2.0 to about 1.0.

13. The antiperspirant composition of claim 12 wherein the ClogP value is from about –1.0 to about 0.5.

14. The composition of claim 9 wherein the composition contains from about 5% to about 80% by weight of isopropyl glycerol ether.

15. The antiperspirant composition of claim 1 wherein the composition comprises from about 0.1% to about 35% by weight of the solubilized antiperspirant active.

16. The antiperspirant composition of claim 1 wherein the composition is visibly clear or translucent at 25° C.

17. The antiperspirant composition of claim 1 wherein the composition further comprises about 10% to about 90% by weight of a volatile silicone.

18. The antiperspirant composition of claim 17 wherein the composition further comprises a nonvolatile silicone.

19. The antiperspirant composition of claim 1 wherein the composition contains less than 5% by weight of water.

20. The antiperspirant composition of claim 1 wherein the solubilized antiperspirant active is selected from the group consisting of aluminum salts, zirconium salts, and combinations thereof.

21. The antiperspirant composition of claim 1 wherein the composition further comprises a suspending or thickening agent.

22. A method of controlling malodor associated with perspiration comprising the topical application to the axillary area of an effective amount of the antiperspirant composition of claim 1.

23. An anhydrous antiperspirant composition comprising:
   A) from about 5% to about 80% by weight of a isopropyl glycerol ether;
   B) from about 5% to about 20% by weight of solubilized antiperspirant active selected from the group consisting of aluminum containing material, aluminum-zirconium materials, and combinations thereof;
   C) less than 5% by weight of water;
   D) a water-soluble, neutral amino acid; and
   E) an acid selected from the group consisting of aluminum chloride, hydrochloric acid, and combinations thereof;
wherein the mole ratio of the neutral amino acid to the zirconium and aluminum is from about 0.09 to about 0.24, the mole ratio of the isopropyl glycerol ether to the aluminum and zirconium is at least about 2.0:1, and the mole ratio of the zirconium and aluminum to chlorine is less than about 1.30:1.

24. The anhydrous antiperspirant composition of claim 23 wherein the water soluble amino acid is glycine.

25. The antiperspirant composition of claim 23 wherein the mole ratio isopropyl glycerol ether to the aluminum and zirconium is at least about 2.0:1.

26. The antiperspirant composition of claim 23 wherein the mole ratio of the isopropyl gylcerol ether to the aluminum and zirconium is at least about 3.0:1.

27. The antiperspirant composition of claim 23 wherein the composition further comprises from about 0.1% to about 35% by weight of a suspending or thickening agent and from about 10% to about 90% by weight of a volatile silicone.

28. An anhydrous antiperspirant composition comprising:
   A) from about 0.1% to about 50% by weight of solubilized antiperspirant active selected from the group consisting of aluminum containing materials, aluminum-zirconium containing materials, and combinations thereof;
   B) from about 0.1% to about 99.9% by weight of a liquid polyol having at least two hydroxyl groups, wherein 2 of the hydroxyl groups are attached to the α and β carbons of the liquid polyol and no more than 4 of the hydroxyl groups are attached to adjacent carbon atoms, wherein the liquid polyol has a C log P value of from about −4.0 to about 2.0, and wherein the liquid polyol has a general formula selected from the group consisting of:

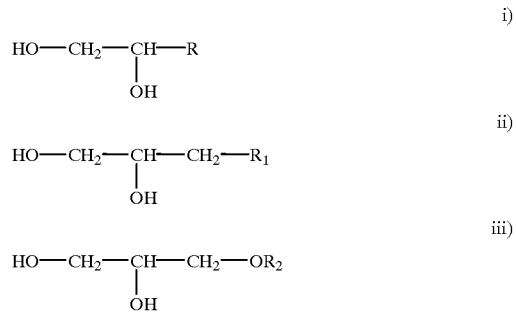

and combinations thereof; wherein R, $R_1$ and $R_3$ are selected from the group consisting of substituted or unsubstituted, branch or straight or cyclic, saturated or unsaturated, alkyl groups, and combinations thereof;
   C) a water-soluble, neutral amino acid; and
   D) a chlorine-containing inorganic acid;
wherein the mole ratio of the neutral amino acid to the zirconium and aluminum is from about 0.09 to about 0.24, the mole ratio of the liquid polyol to the aluminum and zirconium is at least about 2.0:1, and the mole ratio of the zirconium and aluminum to chlorine is less than about 1.30:1.

29. The anhydrous antiperspirant composition of claim 28 wherein the water soluble amino acid is glycine.

30. The antiperspirant composition of claim 28 wherein the mole ratio of liquid polyol to the aluminum and zirconium is at least about 3.0:1.

31. The antiperspirant composition of claim 28 wherein the liquid polyol conforms to formula (i) wherein R is selected from the group consisting of ethyl, and alkyl groups having from 4 to 6 carbon atoms.

32. The antiperspirant composition of claim 28 wherein the liquid polyol is an alkyl diol that conforms to formula (ii) wherein $R_1$ is selected from the group consisting of methyl, and alkyl groups having from 3 to 5 carbon atoms.

33. The antiperspirant composition of claim 28 wherein the liquid polyol is a glycerol ether that conforms to formula (iii) wherein $R_3$ is an alkyl group having from 1 to 5 carbon atoms.

34. The antiperspirant composition of claim 28 wherein the chlorine-containing inorganic acid is selected from the group consisting of aluminum chloride, hydrochloric acid and combinations thereof.

* * * * *

UNITED STATES PATENT AND TRADEMARK OFFICE
CERTIFICATE OF CORRECTION

PATENT NO.   : 6,126,928
DATED        : October 3, 2000
INVENTOR(S)  : Swaile

It is certified that error appears in the above-identified patent and that said Letters Patent is hereby corrected as shown below:

<u>Column 18,</u>
Line 51, "1,2-glycerin;" should read -- 1,2-hexandiol; glycerin; --.

Signed and Sealed this

Twenty-sixth Day of February, 2002

Attest:

Attesting Officer

JAMES E. ROGAN
Director of the United States Patent and Trademark Office